United States Patent [19]

Ammon et al.

[11] Patent Number: 5,401,777
[45] Date of Patent: Mar. 28, 1995

[54] USE OF PREPARATIONS OF CURCUMA PLANTS

[75] Inventors: H. P. T. Ammon; Hasan Safayhi, both of Tübingen; Samuel N. Okpanyi, Wiesbaden, all of Germany

[73] Assignee: Steigerwald Arzneimittelwerk GmbH, Darmstadt, Germany

[21] Appl. No.: 974,056

[22] Filed: Nov. 10, 1992

[51] Int. Cl.⁶ .............................................. A61K 31/05
[52] U.S. Cl. .................... 514/731; 514/886; 514/925
[58] Field of Search .................... 514/731, 886, 925

[56] References Cited

PUBLICATIONS

M. Wichtl (1989) "Teedrogen" second edition, pp. 191-192, 297-298.
G. Madaus (1938) "Heilpflanzen", vol. II, pp. 1151-1156.
Ammon, et al. (1992) Curcumin: a potent inhibitor of leukotriene B₄ formation in rat peritoneal polymorphonuclear neutrophils (PMNL). Planta Med 58(2):226.
Flynn and Rafferty (1986) Inhibition of human neutrophil 5-lipoxygenase activity by gingerdione, shogaol, capsaicin and related pungent compounds. Prostaglandins Luekot. Med. 24(2-3):195-198.
Flynn and Rafferty (1986) Inhibition of 5-hydroxy-eicosatetraenoic acid (5-hete) formation in intact human neutrophils by naturally-occurring diarlyheptanoids:inhibitiory activities of curcumjinoids and yakuchinones. Prostaglandins Leukot. Med. 22(3):357-360.
Huang, et al. (1991) Inhibitory effects of curcumin on in vitro lipoxygenase and cyclooxygenase activities in mouse epidermis. Cancer Res. 51(3):813-819.
Wagner, et al. (1986) In vitro-Hemmung der Prostaglandin-Biosynthese durch etherische Öle und phenolische Verbindungen. Planta Med No. 3:184-187.
List and Hörhammer (1973) Curcuma. "Hagers Handbuch der Pharmazeutischen Praxis." vol. 4, Springer Verlag, Berlin, pp. 380-389. (An English summary of this reference is provided.).
The Merck Index, 9th ed. 1926 p. 348 No. 2681.

Primary Examiner—John W. Rollins
Assistant Examiner—E. White
Attorney, Agent, or Firm—Bertram I. Rowland

[57] ABSTRACT

The invention relates to the use of preparations of the plant Curcuma longa or other curcumin-containing plants, curcumin or curcumin derivatives for the prophylaxis and/or treatment of conditions associated with excessive formation of leucotrienes and/or prostaglandins and to the use of preparations of the plant Curcuma longa or other curcumin-containing plants, curcumin or curcumin derivatives for the production of medicaments for the prophylaxis and/or treatment of conditions associated with excessive formation of leucotrienes and/or prostaglandins.

10 Claims, 3 Drawing Sheets

USE OF PREPARATIONS OF CURCUMA PLANTS

DESCRIPTION

This invention relates to the use of preparations of the plant *Curcuma longa* or other curcumin-containing plants, curcumin or curcumin derivatives for the prophylaxis and/or treatment of conditions associated with excessive formation of leucotrienes and/or prostaglandins. The invention also relates to the use of preparations of the plant *Curcuma longa* or other curcumin-containing plants, curcumin or curcumin derivatives for the preparation of medicaments for the prophylaxis and/or treatment of conditions associated with excessive formation of leucotrienes and/or prostaglandins.

According to the invention, the preparations are used in particular for inflammatory bowel diseases, such as ulcerative colitis or Crohn's disease, and for chronic hepatitis, chronic bronchial asthma or psoriasis.

Crohn's disease and ulcerative colitis, for example, are two chronically inflammatory bowel conditions which cannot be influenced sufficiently, if at all, with hitherto available therapy. From the pathophysiological viewpoint, it is assumed that excessive formation of so-called leucotrienes (inflammatory mediators which act in particular as attractants for white blood cells) are the main reason why these conditions persist. Hitherto, there has been virtually no effective medication for inflammatory bowel diseases. Although so-called glucocorticoids (derivatives of adrenal cortex hormones), more particularly cortisone, are available, they have serious side effects so that their use is not without problems. The application of sulfasalazine is also unsatisfactory. Sulfasalazine is a substance which mainly inhibits the formation of so-called prostaglandins which are also inflammatory mediators. However, the role of prostaglandins in the inflammatory process is basically different from that of leucotrienes. The inhibition of prostaglandin synthesis does not give the required result by these diseases.

Chronic asthma and psoriasis are diseases for which there has hitherto been no satisfactory medication. Both are treated inter alia with cortisone or cortisone derivatives. However, the administration of cortisone and its derivatives, particularly over prolonged periods, is accompanied with considerable disadvantages. Chronic hepatitis cannot be satisfactorily treated either.

It is known that cell membrane constituents contain phospholipids. Arachidonic acid is eliminated from phospholipids of the cell membranes by phospholipase A2 and is in turn converted into prostaglandins and leucotrienes by cyclooxygenase and lipoxygenase. The prostaglandins and the leucotrienes cause inflammation to persist in chronic inflammatory bowel conditions, in chronic hepatitis, chronic bronchial asthma or psoriasis.

The problem addressed by the present invention was to provide a use for preparations intended for the prophylaxis and/or treatment of conditions associated with excessive formation of leucotrienes and/or prostaglandins. The preparations used in accordance with the invention would have low toxicity and would be readily tolerated by patients and, in addition, would be readily available.

It has surprisingly been found that curcumin or its derivatives or preparations of the plant *Curcuma longa* or other curcumin-containing plants inhibit the inflammatory conditions which are caused by formation of leucotrienes and prostaglandins.

Accordingly, the present invention relates to the use mentioned above.

Figure 1:
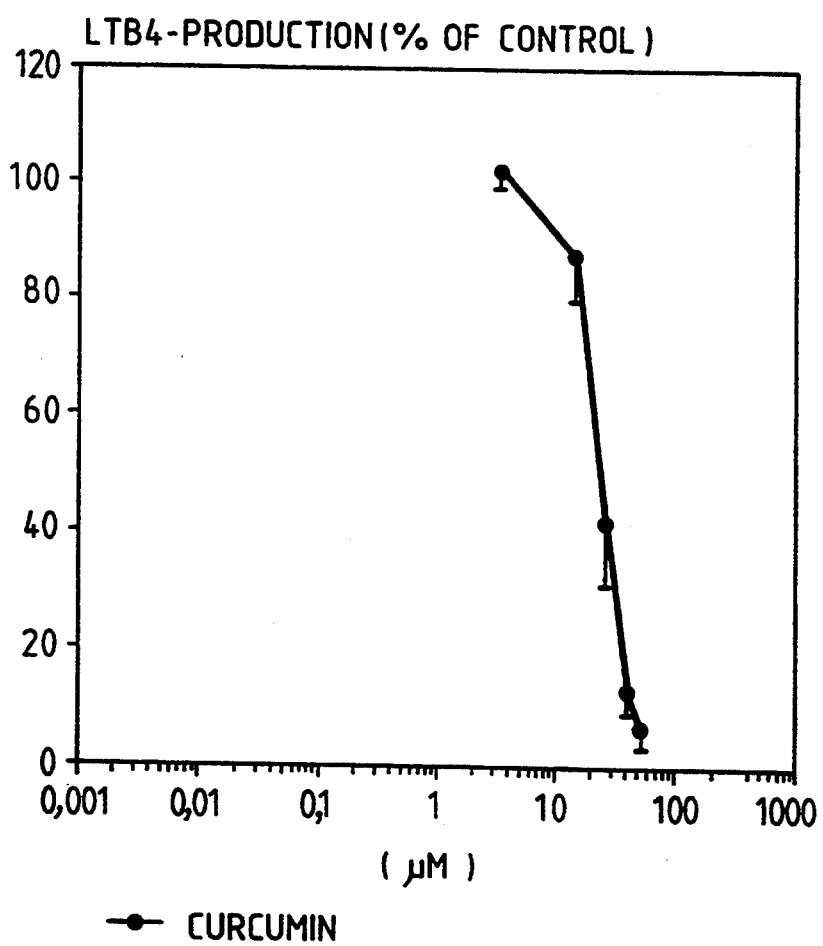
FIG. 1 shows the concentration/effect relation for the inhibition by curcumin of the production of leucotriene B4 from endogenous substrate in intact neutrophilic granulocytes or rats (method: Safayhi, Tiegs, Wendel: Biochem. Pharmacol. 34:2691–2694, 1985).
Figure 2:
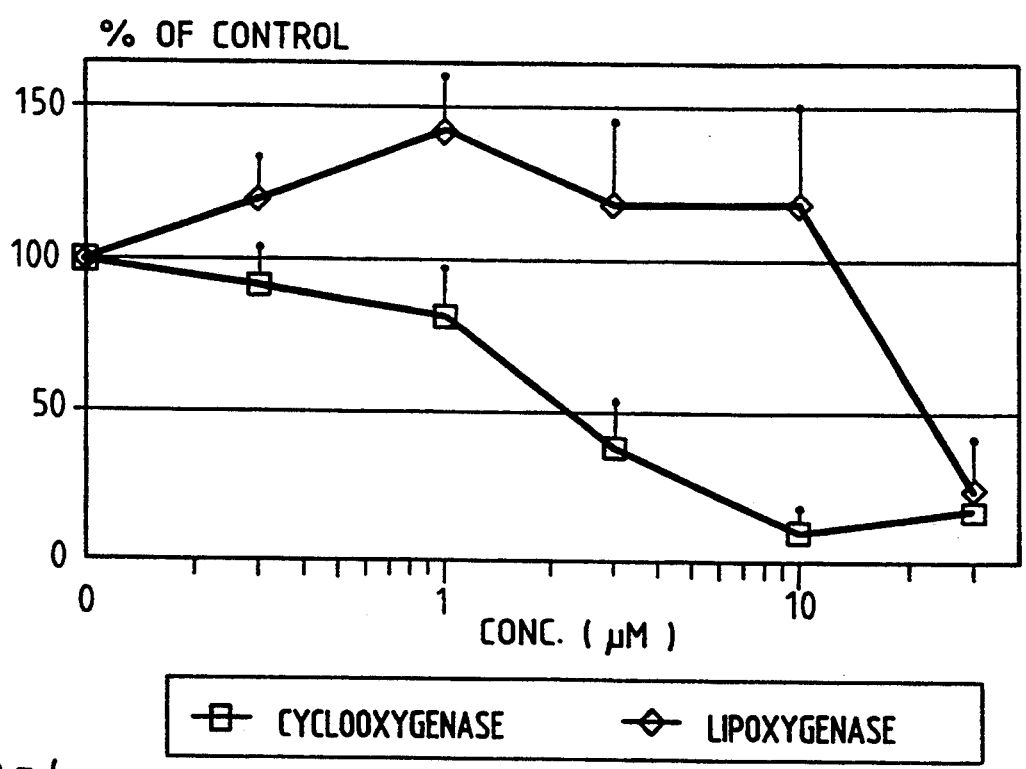
FIG. 2 shows the concentration/effect relation for inhibition of the cyclooxygenase activity in intact blood platelets by curcumin.
Figure 3:
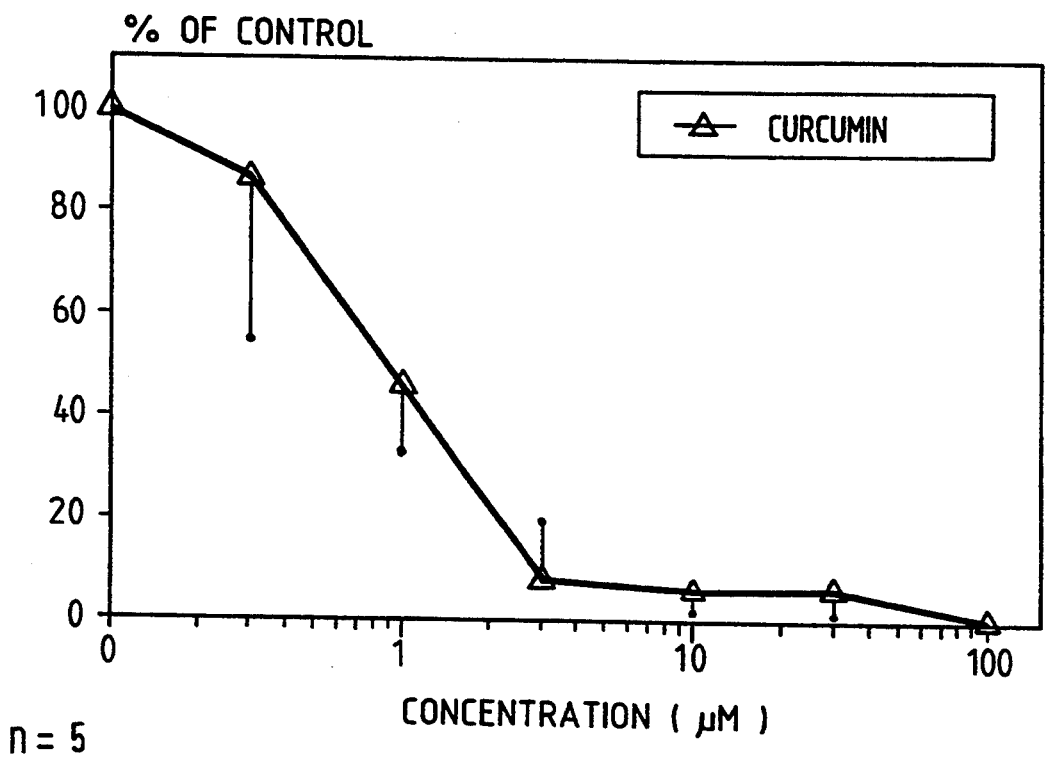
FIG. 3 shows the inhibition by curcumin of Fe/ascorbate-induced formation of oxidized products of arachidonic acid.

Applicants have carried out pharmacological tests in conjunction with investigations into the mechanism of the general antiinflammatory effect described with reference to the animal model of rat paw edema (overview in Ammon and Wahl, 1990)—and obtained the following biochemical results:

Curcumin inhibits in vitro the activity:

(a) of the key enzyme in the biosynthesis of leucotrienes (5-lipoxygenase) in stimulated neutrophilic granulocytes of rats with a semi-maximal inhibiting concentration ($IC_{50}$) of approx. 20 $\mu$mol/l. FIG. 1 shows the concentration/effect relation for the inhibition by curcumin of the production of leucotriene B4 from endogenous substrate in intact neutrophilic granulocytes of rats [method: Safayhi, Tiegs, Wendel: Biochem. Pharmacol. 34:2691–2694, 1985];

(b) of the key enzyme in the biosynthesis of prostanoids (prostaglandin/thromboxan/prostacyclin) in intact, stimulated human blood platelets with an $IC_{50}$ of approx. 2 $\mu$mol/l. FIG. 2 shows the concentration/effect relation for inhibition of the cyclooxygenase activity in intact blood platelets by curcumin (method: Safayhi et al., JPET 261:1143–1146, 1992);

(c) of 12-lipoxygenase in intact stimulated human blood platelets with an $IC_{50}$ of approx. 20 $\mu$mol/l. FIG. 2 shows the concentration/effect relation for the inhibition by curcumin of the formation of 12-hydroxyeicosatetraenoic acid (12-HETE) in intact human blood platelets (method: Safayhi et al., JPET 261:1143–1146, 1992);

(d) the formation of peroxidized arachidonic acid products in the cell-free system with an $IC_{50}$ of approx. 1 $\mu$mol/l. FIG. 3 shows the inhibition by curcumin of Fe/ascorbate-induced formation of oxidized products of arachidonic acid (method: Safayhi et al., JPET 261:1143–1146, 1992).

These results show that curcumin inhibits the formation of inflammation-promoting mediators from arachidonic acid (leucotrienes via 5-lipoxygenase, 12-HETE via 12-lipoxygenase and prostaglandins via cyclooxygenase) in intact cells and suppresses the formation of toxic peroxides. (a) to (d) represent the combination of inflammation-inhibiting mechanisms of one and the same substance for which nothing comparable is available on the medication market. The discovery of the existence of this combination is also regarded as an invention for the therapy of the conditions mentioned above. Although the increased formation of leucotrienes may be very much in the foreground in the conditions mentioned above, it is important not to overlook the fact that other inflammation mediators, such as prostaglandins and oxygen radicals, also have an inflammation-promoting effect (they are eliminated by the anti-oxidative properties of curcumin). Important inflammatory mediators are summarized in the following Table.

*longa* or other curcumin-containing plants or curcumin derivatives inhibit the formation both of prostaglandins and of leucotrienes, i.e. are comparable in their action profile with the steroids regarding antiinflammatory properties, but do not have the undesired side effects of steroids, particularly of cortisone. This is illustrated below:

TABLE 1

Mediators and their effects. The most important effects for pathophysiological processes are emphasized.

| | Vessel tone | Vessel permeability | Platelet aggregation | Leucocytes | Bronchia | Stomach | Uterus | Pain |
|---|---|---|---|---|---|---|---|---|
| Histamine | Dilation* Constriction* | Increase | | | Constriction | Increase in acid production | Contraction** Relaxation** | Initiation |
| 5-Hydroxytryptamine | Dilation* Constriction* | Increase** | Promotion | | Constriction** | | Contraction* | Initiation |
| Bradykinine | Dilation | Increase | | | Constriction | | Contraction* | Initiation |
| C5a | Contraction | Increase | Promotion | Chemotaxis | Constriction | | | Initiation |
| PGE$_2$ | Dilation | Increase+ | Inhibition° | | Dilation | Protection | | Initiation+ |
| PGF$_{2a}$ | Contraction° | | | | Constriction | | Contraction | |
| PGD$_2$ | Contraction | | Inhibition | Chemotaxis | Constriction | | | Initiation+ |
| PGI$_2$ | Dilation | Increase+ | Inhibition | | | | | |
| TXA$_2$ | Contraction | | Promotion | | Constriction | | | |
| LTB$_4$ | | Increase*** | | Chemotaxis | | | | |
| LTC$_4$ | Contraction | Increase+ | | | Constriction | | | |
| LTD$_4$ | Contraction | Increase+ | | | Constriction | | | |
| PAF | Contraction | Increase | Promotion | Chemotaxis | Constriction | Ulcerative effect | | |
| $-O_2^-$ | Dilation | Increase*** | Chemotaxis | | | | | |

*In dependence upon the circulation section and the animal species
**In dependence upon the animal species
+In the presence of other mediators (e.g. histamine, C5a)
***In the presence of neutrophilic granulocytes
°Only in high concentrations The following diagram illustrates the sites of action of pharmaceutical products currently available on the market with which the inflammatory processes can be influenced within the so-called arachidonic acid cascade:

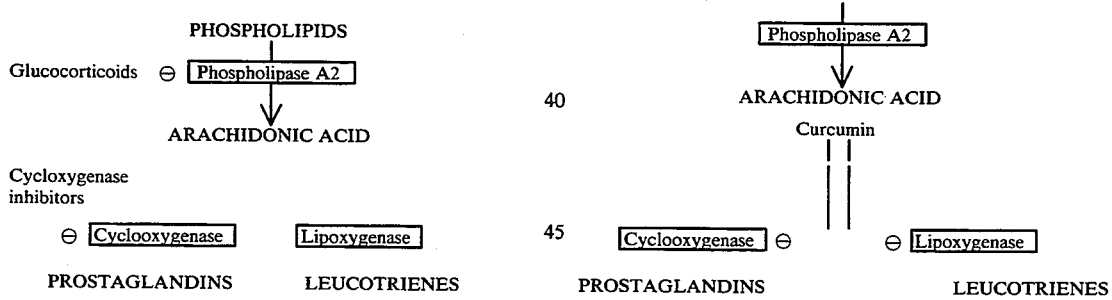

Glucocorticoids

Glucocorticoids inhibit the formation both of prostaglandins and of leucotrienes. However, as derivatives of steroid hormones, they have many serious side effects, as mentioned above.

Nonsteroidal Antiinflammatories

Nonsteroidal antiinflammatories (acetyl salicylic acid, indometacin, diclofenac, ibuprofen, etc.) inhibit the biosynthesis of prostaglandins by action in the region of cyclooxygenase. However, it is precisely because of this that they can lead indirectly to the increased synthesis of leucotrienes and hence can even intensify leucotriene-mediated pathophysiological reactions (example: so-called aspirin asthma). Both classes of inhibitors (glucocorticoids) lack the protective effect of a peroxidation-inhibiting component.

It has surprisingly been found that curcumin and curcumin-containing preparations of the plant *Curcuma*

However, the mode of action of curcumin is basically different from that of steroid hormone congeners. Curcumin does additionally possess an antioxidative action component which can be expected to give an additional curative effect in the inflammation process. Since curcumin is not a hormone, the undesired hormone-induced glucocorticoidal side effects are not present either, although the desired steroidal effects are attained in inflammation-inhibiting activity.

Accordingly, curcumin intervenes in the inflammation process in three ways: its antioxidative effect, which is already achieved in a concentration of only 1 μm, would result in the following:

1. The antioxidative effect eliminates activated oxygen molecules and radicals. There has hitherto been no medicament for such an effect.
2. The antioxidative effect would appear to inhibit the formation of cyclooxygenase products.
3. The formation of 5- and 12-lipoxygenase products is inhibited by the antioxidative effect.

Accordingly, curcumin is a totally new type of antiphlogistic. Its advantage is that, in addition to the activated oxygen species involved in any inflammation process and the cyclooxygenase products, it also inhibits the formation of leucotrienes.

It was surprising to find that curcumin appeared to be effective in the conditions mentioned above, particularly in inflammatory bowel conditions. According to the literature, curcumin does not cure experimental stomach ulcers in rats. Bhatia et al. (Bhatia, A., Singh, G. B. and Khanna, N. M. (1964), Indian J. Exptl. Biol. 2, 58–160) did not find any protective effect of curcumin against histamine-induced stomach ulcers in guinea pigs. In addition, Prasad et al. (Prasad, D. N., Gupta, B., Srivastava, R. K. and Satyavati, G. V. (1976), Indian J. Physiol. Pharmacol. 20, 92) found that high doses of curcumin damaged the stomach mucosa when curcumin was orally administered in daily doses of 100 mg/kg over a period of 6 days.

Prostaglandins in physiological concentrations protect the stomach mucosa. Prostaglandins do not have a protective effect on the intestinal mucosa (as opposed to the stomach mucosa). Accordingly, the synchronous inhibition of the inflammation mediators (prostaglandins and leucotrienes) and inhibition of the formation of peroxides by curcumin, particularly in cases of inflammation of the intestinal mucosa (ulcerative colitis and Crohn's disease) was surprising to the expert in this combination.

Preparations of the plant *Curcuma longa*, preferably preparations obtained from roots or rhizomes, preparations of other plants containing curcumin, for example *Curcuma longa* L. (syn. *Amomum curcuma* Jacq., *Curcuma domestica* Lour., *Curcuma xanthorrhiza* Naves), *Curcuma xanthorrhiza* Roxb. (syn. *Curcuma xanthorrhiza* Dietrich, *Curcuma xanthorrhiza* Roxb.), natural or synthetic curcumin or curcumin derivatives are used in accordance with the invention. Curcumin is the principal ingredient of the so-called yellowroot (*Curcuma longa*) and of *Curcuma xanthorrhiza*. The yellowroot has long been used in Asian countries, especially for the treatment of dyspepsia (indigestion without closer characterisation). It is also an ingredient of the curry spice familiar to everyone.

The following drugs contain sesquiterpenes in which curcumin can also be present: *Curcuma aromatica* Salisb. (syn. *Curcuma zeodaria* Roxb.), Curcuma Kwandsiensis Lee et Liang, *Curcuma zedoaria* (Berg.) Rosc. (syn. *Amomum zedoaria* Berg., *Amomum zerumbet* Koen., *Costus luteus* Blanco, *Curcuma nigricans* Blanco, *Curcuma zerumbet* Roxb., *Roscoea lutea* Hassk., *Roscoea nigrociliata* Hassk.). These substances may also be used in accordance with the invention providing they contain curcumin.

In addition, curcumin as such is scarcely found in the blood after peroral administration. Accordingly, curcumin is particularly suitable for local application [psoriasis, chronic bronchial asthma (spray, inhalant)]. Since curcumin is found in the liver (Ammon and Wahl, 1990), it may also be used in the treatment of chronically inflammatory hepatitis.

In the treatment of conditions where the synthesis of leucotriene is increased and against which curcumin is not effective after oral administration, parenteral administration or the application of resorbable derivatives with a minimal "first pass" effect should be considered.

Curcumin has the following formula:

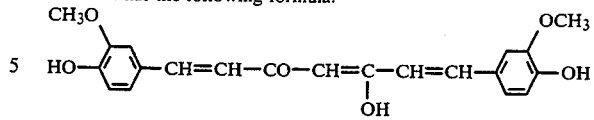

Curcumin has hardly any toxic effects when orally administered in doses of 5 g/kg to guinea pigs and rats.

The preparations according to the invention are suitable for intraperitoneal, oral, rectal, intramuscular, topical, subcutaneous, intraarticular or intravenous administration. Oral administration is preferred. The preparations according to the invention may be used in the form of tablets, dragees, capsules, solutions, emulsions, ointments, creams, inhalants, aerosols or suppositories.

According to the invention, the preparations may be used together with other chemically pure medicinal substances and/or other plant-based medicaments.

The following are examples of other chemically pure medicinal substances:

BRONCHOLYTICS AND ANTIASTHMATICS

SYMPATHOMIMETICS:
Carbuterol HCl
Clenbuterol HCl
Fenoterol HBr
Isoetarin HCl
Orciprenalin sulfate
Pirbuterol HCl
Procaterol HCl
Reproterol HCl
Sabutamol sulfate
Terbutalin sulfate
Tulobuterol HCl

ANTIPSORIATICS

NONSTEROIDAL ANTIPHLOGISTICS:
Salicylic acid and derivatives
VITAMINS:
Folic acid
Vitamin E
Vitamin B12
Vitamin A
VARIOUS:
Cadmium sulfide
Benzalkonium chloride
Sodium bituminosulfonate
Armmoidin
Allantoin
Methotrexat
Paraffin
Tioxolon
Dithranol
Fumaric acid
Undecylenic acid
Polyoxyethylene lauryl ether sulfate
Etretinat
Zinc oxide
Urea
Lactic acid The preparations used in accordance with the invention may be formulated in known manner using one or more pharmaceutically acceptable vehicles or diluents. The preparations may be formulated for oral, parenteral rectal or intranasal administration or in a form suitable for administration by inhalation or insufflation. Preparations of the compounds for oral administration are preferred.

The pharmaceutical preparations for oral administration may be formulated, for example, as tablets or capsules which may be produced by methods known per se with pharmaceutically acceptable diluents, such as binders (for example pregelatinized cornstarch, polyvinyl pyrrolidone or hydroxypropyl methyl cellulose), fillers (for example lactose, sucrose, mannitol, cornstarch, microcrystalline cellulose or calcium hydrogen phosphate); lubricants (for example stearic acid, polyethylene glycol, magnesium stearate, talcum or silicon dioxide); disintegrating agents (for example potato starch, sodium starch glycolate or sodium carboxymethyl cellulose); or wetting agents (for example sodium lauryl sulfate). The tablets may be coated by methods known per se. Liquid preparations for oral administration may be present in the form of, for example, aqueous or oily solutions, syrups, elixirs, emulsions or suspensions, or alternatively may be present as a dry product for constitution with water or another suitable medium before use. Preparations such as these may be produced by methods known per se with pharmaceutically acceptable additives, such as suspending agents (for example sorbitol syrup, cellulose derivative, glucose/sugar syrup, gelatine, aluminum stearate gel or hydrogenated edible fats); emulsifiers (for example lecithin, acacia or sorbitan monooleate); non-aqueous vehicles (for example almond oil, oily esters, ethyl alcohol or fractionated vegetable oils); and preservatives (for example methyl or propyl p-hydroxybenzoates or sorbic acid). If desired, the liquid preparations may also contain buffers, flavorings, dyes and sweeteners known per For parenteral administration, the compounds may be formulated by injection, preferably intravenous, intramuscular or subcutaneous injection. Preparations for injection may be present in dose unit form, for example in ampoules or multiple-dose containers, with an added preservative. The preparations may be present in the form of suspensions, solutions or emulsions in oily or aqueous vehicles and may contain formulation aids, such as suspending agents, stabilizers and/or dispersants, and/or agents for adjusting the tonicity of the solution. Alternatively, the active constituent may be present before use in powder form for constitution with a suitable vehicle, for example sterile pyrogen-free water.

The compounds may also be formulated as rectal preparations, such as suppositories, for example those containing suppository bases known per se, such as cocoa butter or other glycerides.

For intranasal administration, the compounds may be used as liquid sprays or in the form of drops.

For administration by inhalation, the compounds are best dispensed in the form of an aerosol spray from a pressurized pack using suitable propellents or in an atomizer. Where a pressurized aerosol is used, the dose unit is determined by the provision of a valve which releases a measured quantity. Capsules and cartridges, for example of gelatin, for use in an inhaler or in an insufflation device may be prepared in such a way that they contain a powder mixture of a compound used in accordance with the invention and a suitable powder base, such as lactose or starch.

The use according to the invention is illustrated by the following Examples.

Example 1

| Tablets for oral administration | |
|---|---|
| A. Direct compression | |
| (1) | |
| Active principle: curcumin derivative | 15–30 mg/tablet |
| (or powdered drug | 0.5–1.0 g/tablet) |
| Magnesium stearate BP | 0.65 mg/tablet |
| Anhydrous lactose | 80 mg/tablet |
| The active principle is mixed with the anhydrous lactose and the magnesium stearate and the mixture is sieved. The mixture formed is compressed to tablets using a tabletting machine. | |
| (2) | |
| Active principle: curcumin derivative | 15–30 mg/tablet |
| (or powdered drug | 0.5–1.0 g/tablet |
| Magnesium stearate B | 0.7 mg/tablet |
| Microcrystalline cellulose NF | 100 mg/tablet |
| The active principle is sieved and mixed with the microcrystalline cellulose and the magnesium stearate. The mixture formed is compressed to tablets using a tabletting machine. | |
| B. Wet granulation | |
| Active principle: curcumin derivative | 15–30 mg/tablet |
| (or powdered drug | 0.5–1.0 g/tablet) |
| Lactose BP | 150.0 mg/tablet |
| Starch BP | 30.0 mg/tablet |
| Pregelatinized cornstarch BP | 15.0 mg/tablet |
| Magnesium stearate BP | 1.5 mg/tablet |

The active principle is sieved through a suitable sieve and mixed with the lactose, the starch and the pregelatinized cornstarch. Suitable volumes of purified water are added and the powder is granulated. After drying, the granules are sieved and mixed with the magnesium stearate. The granules are then pressed to tablets using punch presses with a suitable diameter.

Tablets of different composition can be produced by varying the ratio of active principle to lactose or the compression weight and using corresponding punch presses.

Example 2

| Capsules | |
|---|---|
| Active principle: curcumin derivative | 15–30 mg/capsule |
| (or granulated drug | 0.5–1.0 g/capsule) |
| Starch 1500 | 150.00 mg/capsule |
| Magnesium stearate BP | 1.00 mg/capsule |

The active principle is sieved and mixed with the other constituents. The mixture is introduced into No. 2 hard gelatine capsules using a suitable machine. Other capsules can be produced by changing the filling weight and, if necessary, changing the capsule size accordingly.

Example 3

| Syrup | |
|---|---|
| Sucrose-free preparation | mg/5 ml dose |
| Active principle: curcumin derivative | 15–30 |
| Hydroxypropyl methyl cellulose USP (viscosity type 4000) | 22.5 |
| Buffer<br>Flavoring<br>Dye<br>Preservative<br>Sweetener | As required |

-continued

| Syrup | |
|---|---|
| Sucrose-free preparation | mg/5 ml dose |
| Purified water to | 5.0 ml |

The hydroxypropyl methyl cellulose is dispersed in hot water, cooled and then mixed with an aqueous suspension containing the active principle and the other components of the preparation. The solution formed is adjusted to its volume and mixed.

Example 4

| Suspension | mg/5 ml dose |
|---|---|
| Active principle: curcumin derivative (or powdered drug (corresponding to dried drug extract) | 15–30 0.5–1.0 g) |
| Aluminum monostearate | 75.00 |
| Sweetener Flavoring Dye | As required |
| Fractionated coconut oil to | 5.00 |

The aluminium monostearate is dispersed in approximately 90% of the fractionated coconut oil. The resulting suspension is heated with stirring to 115° C. and then cooled. The sweetener, flavoring and dye are then added and the active principle is dispersed. The suspension is adjusted to its volume with the remaining fractionated coconut oil and mixed.

Example 5

| Sublingual tablet | |
|---|---|
| Active principle: curcumin derivative (or drug extract | 15–30 mg/tablet 0.5–1.0 g/tablet) |
| Compressible sugar NF | 50.5 mg/tablet |
| Magnesium stearate BP | 0.5 mg/tablet |

The active principle is sieved through a suitable sieve, mixed with the other constituents and pressed using suitable punch presses. Tablets of different strength can be produced by changing the ratio of active principle to excipient or the compression weight.

Example 6

| Suppositories for rectal administration | |
|---|---|
| Active principle, curcumin derivative | 15–30 mg |
| Witepsol H15+ to | 1.0 g |

+ Suitable quality of Adeps solidus pH.Eur

A suspension of the active principle in molten Witepsol is prepared and introduced into 1 g suppository molds by a suitable machine.

Example 7

| Injection for intravenous administration | |
|---|---|
| Active principle, curcumin derivative | 15–30 mg |
| Sodium chloride intravenous infusion, BP, 0.9% by weight/vol. to | 1 ml |
| Batch size | 2500 ml |

The active principle is dissolved in part of the sodium chloride intravenous infusion, the solution is adjusted to its volume with the sodium chloride intravenous infusion and the solution is thoroughly mixed. The solution is introduced into clear type 1–10 ml glass ampoules and sealed off under nitrogen in the head space by fusing the glass. The ampoules are sterilized by heating in an autoclave at 120° C. for not less than 20 minutes.

Example 8

| Cartridge for inhalation | |
|---|---|
| Active principle (micronized): curcumin derivative | 15–30 mg/cartridge |
| Lactose BP | 25.00 |

The active principle is micronized to a fine particle size range in an energy mill and then mixed with the lactose. The powder is introduced into No. 3 hardened gelatine capsules.

Example 9

| Nasal spray | |
|---|---|
| Active principle: curcumin | 1.5–3.0 %/vol. |
| Preservative Sodium chloride BP | As required |
| Purified water BP to | 100 |
| Delivery veight | 100 mg (equivalent to 7 mg active principle) |

The active principle, the preservative and the sodium chloride are dissolved in part of the water. The solution is adjusted to its volume with water and thoroughly mixed.

We claim:

1. A method for treatment of a patient susceptible to a condition associated with pathophysiological formation of leucotrienes, the method comprising:
   administering to said patient a pharmacologically effective amount of a preparation comprising curcumin or a curcumin derivative to reduce said formation of said leucotrienes.

2. A method according to claim 1 wherein said preparation is derived from a curcumin-containing plant.

3. A method according to claim 2, wherein said condition is chronic inflammatory bowel disease.

4. A method according to claim 3, wherein said chronic inflammatory bowel disease is ulcerative colitis or Crohn's disease.

5. A method according to claim 2, wherein said condition is chronic hepatitis, chronic bronchial asthma or psoriasis.

6. A method according to claim 1, wherein said inflammatory mediators are at least one of a prostaglandin or leucotriene.

7. A method according to claims 2, 3 or 5, wherein said preparation is formulated for intraperitoneal, oral, rectal, intramuscular, topical, subcutaneous, intraarticular or intravenous administration.

8. A method according to claims 2, 3 or 5, wherein said preparation is in the form of a tablet, dragee, capsule, solution, emulsion, ointment, cream, inhalant, aerosol or suppository.

9. A method according to claims 2, 3 or 5, wherein said preparation further comprises:
   a pharmaceutically effective amount of at least one of a medicinal substance or plant-based medicament other than a curcumin containing plant.

10. A method for treatment of a patient susceptible to ulceralive colitis or Crohn's disease, the method comprising:
    administering to said patient a pharmacologically effective amount of a preparation of the plant *Curcuma longa*.

* * * * *